(12) United States Patent
Herring

(10) Patent No.: US 7,100,421 B1
(45) Date of Patent: Sep. 5, 2006

(54) MICRO-DISCHARGE GAS DETECTOR

(75) Inventor: Cyrus M. Herring, Urbana, IL (US)

(73) Assignee: Caviton, Inc., Champaign, IL (US)

( * ) Notice: Subject to any disclaimer, the term of this patent is extended or adjusted under 35 U.S.C. 154(b) by 0 days.

(21) Appl. No.: 10/241,887

(22) Filed: Sep. 12, 2002

Related U.S. Application Data

(60) Provisional application No. 60/318,774, filed on Sep. 13, 2001.

(51) Int. Cl.
*G01N 30/02* (2006.01)
*G01N 27/62* (2006.01)

(52) U.S. Cl. .................. 73/23.35; 73/23.4; 324/464

(58) Field of Classification Search ............. 73/23.22, 73/23.21, 23.35, 23.39, 23.4; 324/464
See application file for complete search history.

(56) References Cited

U.S. PATENT DOCUMENTS

| | | | | |
|---|---|---|---|---|
| 3,656,339 A | * | 4/1972 | Narain | 73/31.03 |
| 3,920,401 A | * | 11/1975 | Gatiss et al. | 422/54 |
| 4,794,252 A | * | 12/1988 | Bateman et al. | 250/288 |
| 5,036,195 A | * | 7/1991 | Batey et al. | 250/288 |
| 5,153,519 A | * | 10/1992 | Wentworth et al. | 324/464 |
| 5,281,915 A | * | 1/1994 | Takahama et al. | 73/31.05 |
| 5,317,271 A | * | 5/1994 | Wentworth et al. | 324/464 |
| 5,394,091 A | * | 2/1995 | Wentworth et al. | 324/464 |
| 5,591,896 A | * | 1/1997 | Lin | 73/31.05 |
| 5,955,886 A | * | 9/1999 | Cohen et al. | 324/464 |
| 6,457,347 B1 | | 10/2002 | Koo | |

* cited by examiner

*Primary Examiner*—Hezron Williams
*Assistant Examiner*—John Fitzgerald
(74) *Attorney, Agent, or Firm*—Singleton Law Firm, P.C.; Alan R. Singleton

(57) ABSTRACT

A gas detector especially adapted for use with gas chromatographs contains two capillary tubing electrodes through which a gas flows. The inner ends of the electrodes are coaxial and are separated by a gap. The outer end of one of the electrodes forms a gas inlet. The gas detector also contains a coaxial dielectric tube spaced apart from and surrounding the electrodes axially, a means for applying a sufficient voltage across the gap between the electrodes to create a discharge within the gas, and a means for measuring a change in properties of the gas as it passes through the gap between the electrodes.

20 Claims, 3 Drawing Sheets

MICRO-DISCHARGE GAS DETECTOR

CROSS-REFERENCE TO RELATED APPLICATION

This application claims the benefit of U.S. Provisional Application Ser. No. 60/318,774, Sep. 13, 2001.

FIELD OF THE INVENTION

This invention relates to gas detectors. More particularly, this invention relates to micro-discharge gas detectors especially suited for gas chromatograph systems.

BACKGROUND OF THE INVENTION

Gas chromatography is an analytical technique which entails the separation and often identification of individual compounds, or groups of compounds, within a mixture. A gas chromatograph takes a small sample of liquid or gas (typically about 0.1 cubic centimeter), and identifies the amounts of various compounds within the sample, often in the form of a chromatograph. A chromatograph is a line chart with the horizontal axis identifying different compounds and the vertical axis giving the concentration. The total amount of a compound in a given sample is usually related to the area under the peak associated with that particular compound. No other analytical technique is as powerful and as generally applicable as is gas chromatography. It is widely used in most sectors of chemistry, biology, forensics, environmental studies, and many areas of research.

A gas chromatograph is typically composed of three major subsystems: an injection chamber, a column separator, and a gas detector. Each of these subsystems usually has an independent means of temperature control. In order to analyze a sample, it is first injected into the injection chamber where a continual flow or pressure of a carrier gas (hydrogen, helium, nitrogen, air, etc.) is maintained. The injection chamber is usually maintained at a temperature such that various compounds within the sample are vaporized and enter the separation column.

The separation column is a long glass or metal tube which is coated on its interior surface by an inert compound designed to impede the flow of different compounds by different amounts. The separation column is typically about 1 to 30 meters long and has an inner diameter of about 50 microns (μm) to 1 millimeter (mm). Even smaller columns have been fabricated in silicon substrates. The coating is referred to as the packing material and is one of the most important considerations when picking the desired column to analyze a particular sample. The carrier gas carries the evaporated compounds through the column. Different molecules diffuse through the column at different rates even though their stochastic differences may be small. Detailed analysis of compounds often involves the use of several columns with different packing materials.

Many different detection techniques are applied at the exit of the column to help create the desired chromatograph. Most importantly, the detector must be able to distinguish relative changes with respect to time of any physical property of the gas exiting the column. It is not necessarily important for the detector to identify the compounds exiting the column, but instead to be very sensitive to changes in composition of the exiting gas. Each detection system ideally leads to a chromatograph that may have particular advantages over other detectors for specific compounds.

Some of the many types of detectors that are common include flame ionization detectors (FID), flame photometry detectors (FPD), nitrogen phosphorous detectors (NPD), electron capture detectors (ECD), thermal conductivity detectors (TCD), atomic emission detectors (AED), photoionization detectors (PID), electrical conductivity detectors (ELCD), mass spectrometer detectors (MS), discharge ionization detectors (DID), and chemiluminescence detectors.

Some detectors observe properties that can be measured without altering or destroying the gas being detected, such as thermal conductivity detectors. Most detectors, however, require external energy to excite or ionize the gas species, such as all flame-based detectors, ionization detectors and mass spectrometer detectors. These detection techniques often alter the compounds.

Each type of detector has its own advantages and disadvantages. They compete with each other primarily in their sensitivity to given classes of compounds, but also in dynamic range, linearity, universality, portability, and cost. Often compromises among these categories have to be made for specific applications.

A means of converting the observation into an electrical signal is a property of all detectors. Voltage or current is ultimately measured as a function of time and the result displayed on a printout or computer monitor. These results are based on the initial time where the sample was injected into the gas chromatograph. The time between injection and each peak is specific to a particular compound or group of compounds. The instrument is calibrated by injecting a single known compound and measuring the time between the injection and the corresponding peak on the chromatograph. This is repeated for all compounds of interest generating a table of delay times, often referred to as the retention time. The retention time for any compound will ideally be the same even if the compound is contained in a mixture of other compounds. However, these times vary for different columns. Injector chamber and column heating cycles also change the retention times.

Existing gas detectors suffer from several disadvantages. In particular, they are relatively large and consume large amounts of power. Accordingly, there is a demand for a gas detector that is smaller and uses less power.

SUMMARY OF THE INVENTION

The general object of this invention is to provide an improved gas detector. More particular objects are to provide a gas detector that is smaller and uses less power than existing gas detectors. Another object of this invention is to provide an improved gas chromatograph.

I have invented an improved gas detector. The gas detector comprises: (a) two capillary tubing electrodes through which a gas flows, each electrode having an inner end and an outer end, the inner ends of the electrodes being coaxial and separated by a gap, the outer end of one of the electrodes forming a gas inlet; (b) a coaxial dielectric tube spaced apart from and surrounding the electrodes axially; (c) a means for applying a sufficient voltage across the gap between the electrodes to create a discharge within the gas; and (d) a means for measuring a change in properties of the gas as it passes through the gap between the electrodes. I have also invented an improved gas chromatograph having such a gas detector.

The gas detector of this invention is smaller and uses less power than existing gas detectors. Both optical and electrical signals can be measured from the discharge to serve as a time-dependent signal which generates a chromatograph.

Geometrical, optical, and electrical variations can be applied to the device to alter its signal-to-noise ratio, sensitivity, dynamic range, and linearity.

DETAILED DESCRIPTION OF INVENTION

The gas detector of this invention is a micro-hollow-electrode discharge device. The gas detector has two electrodes made of hollow capillary tubing. The electrodes are oriented so their inner ends are coaxial and are separated by a small gap. The gas detector creates an electrical discharge within the carrier gas at the gap between the electrodes. The discharge is characterized by the creation of a plasma. A plasma is electrically conductive due to the relatively high percentage of ions and electrons (electrically charged particles). During this process, the electrons in the atoms and molecules are excited to higher energy levels. As the electrons return to lower energy levels, photons of light are emitted at different wavelengths which are characteristic of the given atoms or molecules. Accordingly, the discharge has different optical and electrical characteristics depending on whether there are any compounds present other than the carrier gas.

Figure 1:
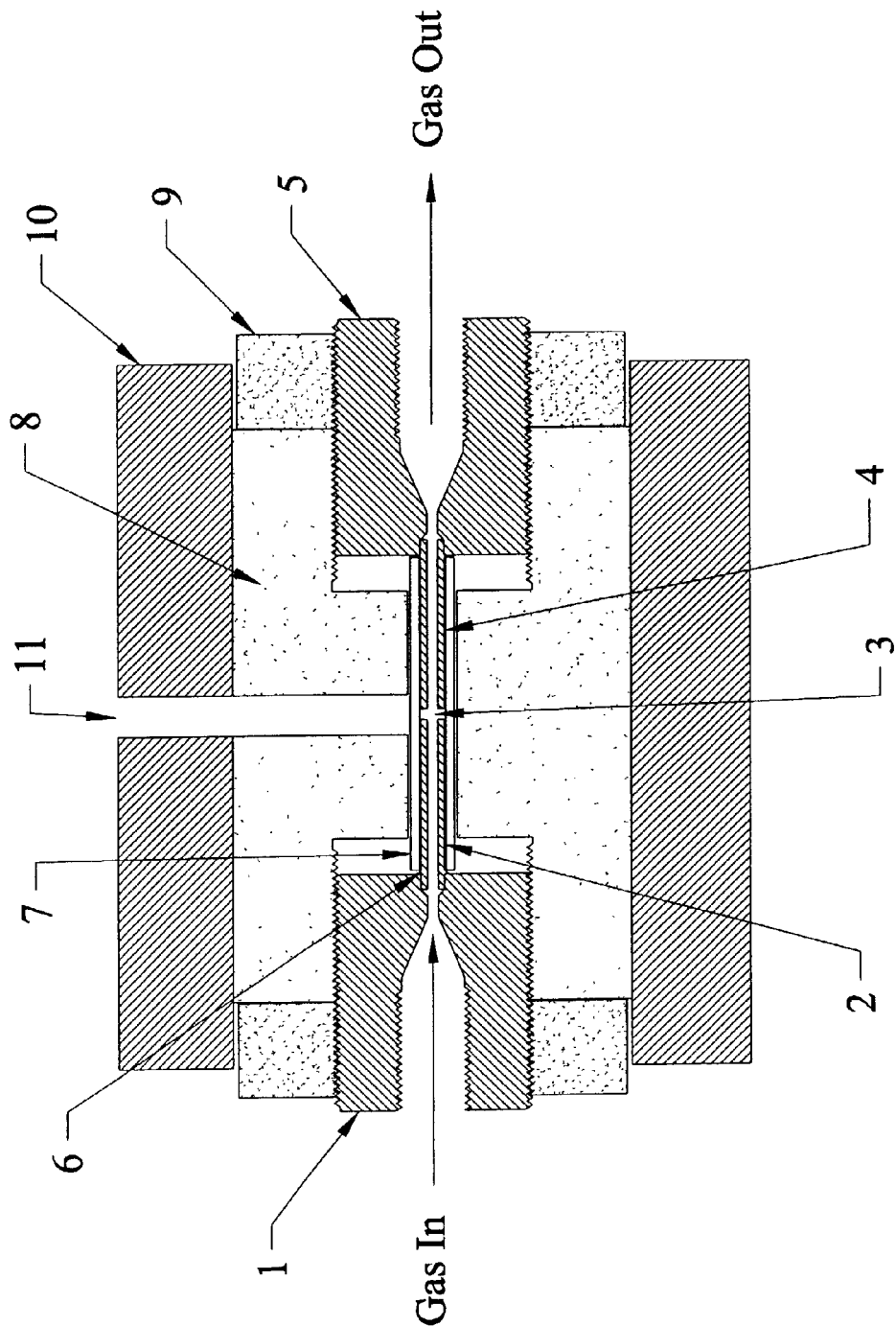
FIG. 1 is a cross section of a first embodiment of the gas detector of this invention.

FIG. 1 shows a cross section of a first preferred embodiment of the gas detector. The gas detector is axially symmetric about the horizontal axis. Gas (for example, from the output of a gas chromatograph column) enters the device through an inlet port 1 which guides the gas into the first electrode 2. The gas then flows through the first electrode, the discharge region 3 at the gap between the two electrodes, and the second electrode 4, before exiting the device through the outlet port 5. The electrode capillary tubes are held in the inlet and outlet ports by a press seal 6 or by similar means such as welds, solders, or the like. A loosely fitting dielectric tube 7 surrounds the capillary tube conductors and helps contain the gas in the discharge region during operation. An electrically insulating body 8 holds the capillary tubes a fixed distance apart at the discharge region and is fixed by the locking rings 9. For lower temperature operation, plastic is suitable for the body. However, for operation at higher temperatures at which plastics melt, a glass-mica-ceramic material is preferable.

A heater 10 brings the device to the desired operating temperature, if desired. The outer portions of the heater must also be electrically insulating to prevent discharges between the inlet and outlet ports. A side port 11 is used to visually set the gap in the discharge region in addition to observing optical properties of the discharge during operation. Multiple ports can be manufactured around the device if necessary. Electrical connections (not shown) are affixed to the locking rings or to the inlet/outlet ports themselves. In addition, a resistive thermocouple device (RTD) or thermocouple can be inserted in the device body for active temperature control.

Figure 2:
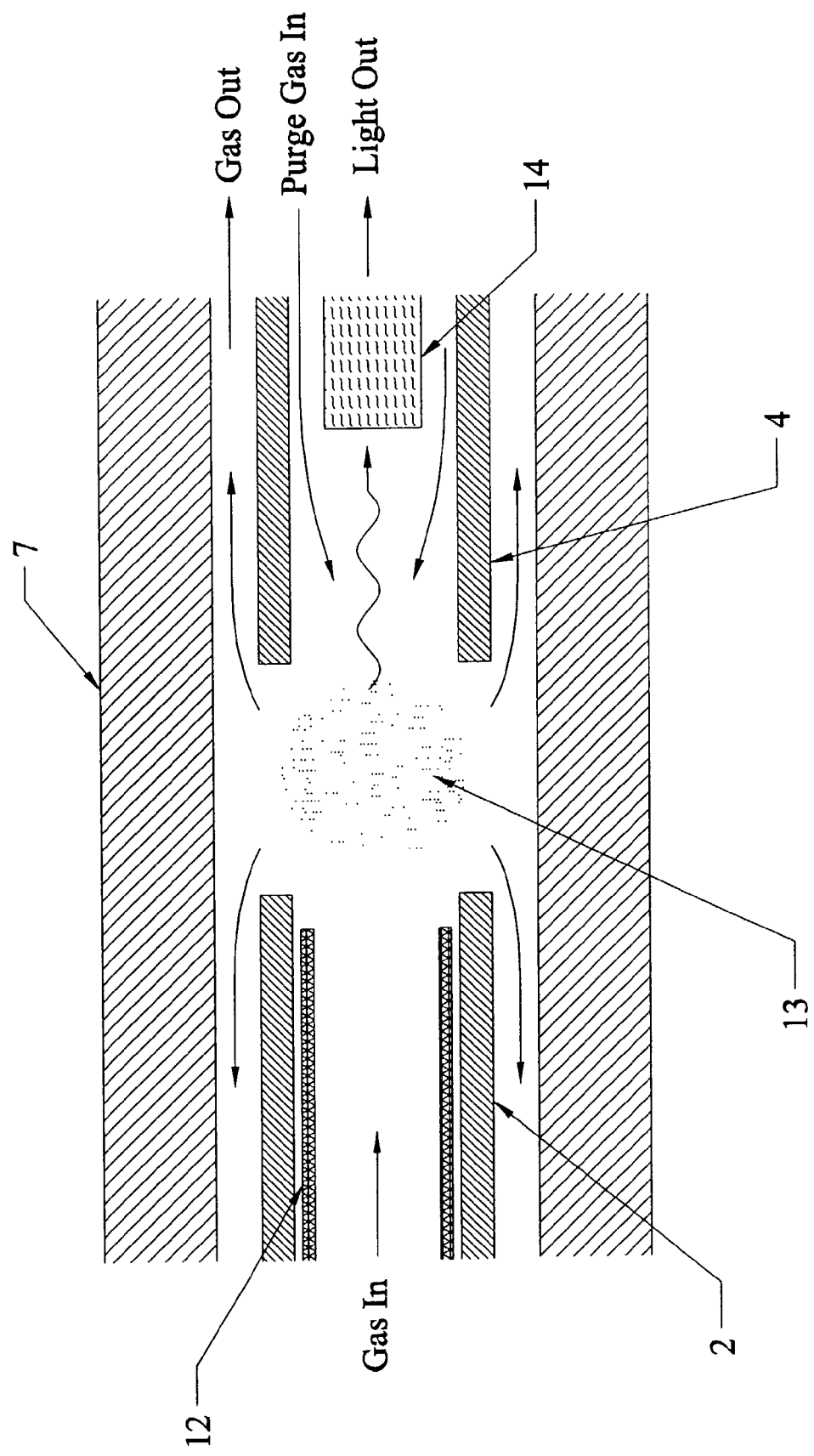
FIG. 2 is a detailed cross section of the discharge region of a second embodiment of the gas detector of this invention.

FIG. 2 is a detailed section of the discharge region of a second preferred embodiment. This embodiment is especially suited for use as part of a gas chromatograph. The output end of the column 12 is inserted inside the first electrode 2. The end of the column extends nearly to the inner end of the electrode so that the gas exiting the column immediately enters the discharge region, represented by sphere 13, at the gap between the electrodes. A fiber optic cable 14 is positioned inside the second electrode 4. The end of the fiber optic cable extends nearly to the inner end of the electrode. The fiber optic cable collects the light emitted by the discharge. In this embodiment, a purge gas such as hydrogen, helium, argon, etc. flows through the second electrode toward the gap. The purge gas is preferably the same as the carrier gas. The purpose of this flow is to prevent any deposits from forming on the end of the fiber optic cable which would decrease optical collection efficiency over time. Gas exits the discharge region through the annular space between the electrodes and the dielectric tube 7. In this embodiment, the dielectric tube can be made of any insulator which allows the exhaust gas to escape.

Figure 3:
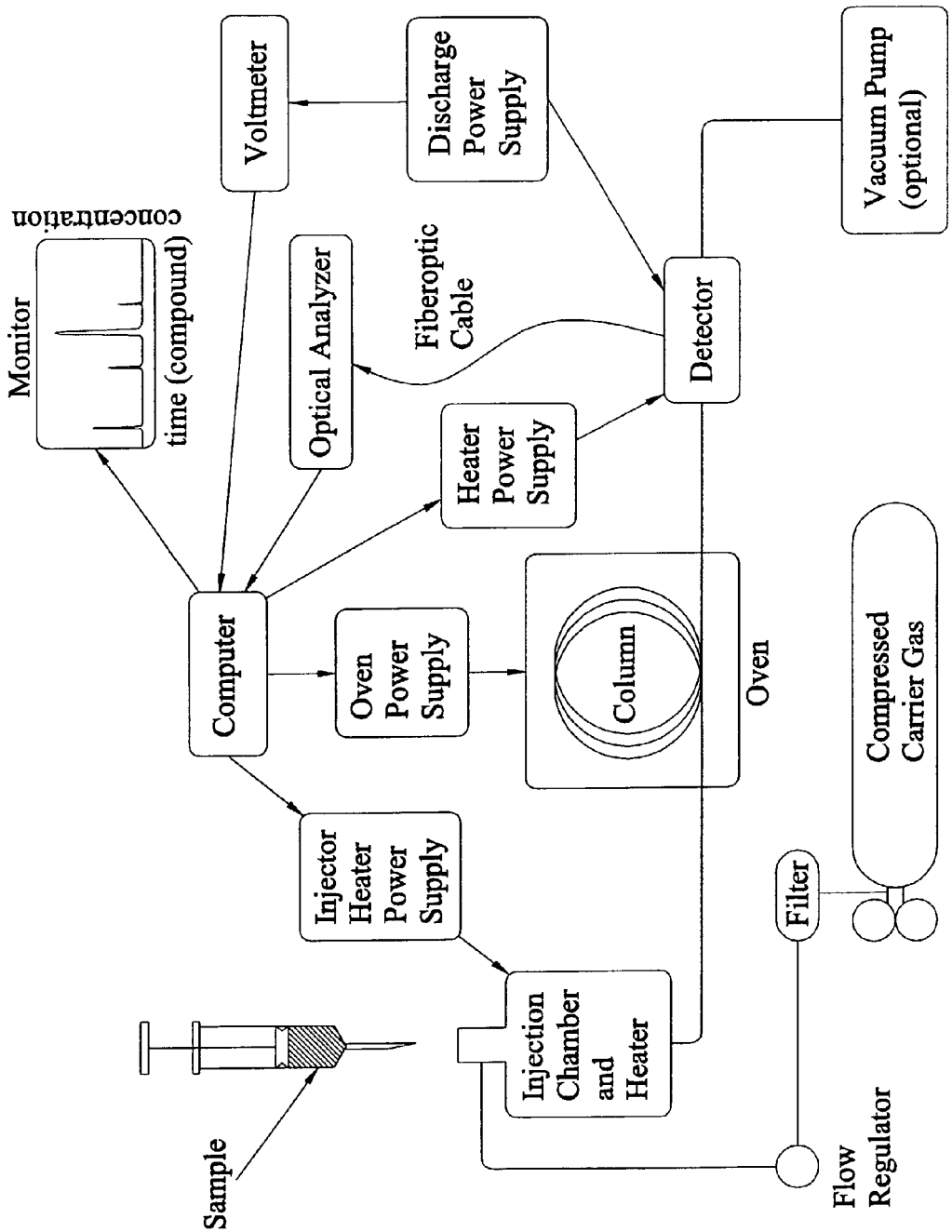
FIG. 3 is a block diagram showing the environment in which the gas detector of this invention is advantageously used.

FIG. 3 is a block diagram of a gas chromatograph showing how the detector may be integrated with the rest of the instrument. Arrows show the flow of power (or information). The heaters and their power supplies are necessary when analyzing liquid samples. However, they can be eliminated when analyzing gaseous samples to make a smaller and more compact gas chromatograph instrument. In addition, this detector technology is inherently small compared with other detectors. Thus, it is suitable for a compact sensitive and universal gas chromatograph detector.

The detector generally operates at a pressure ranging from a few Torr to a few atmospheres. The gap between the electrodes is generally about 10 to 1000 microns, and is preferably about 50 to 500 microns. The inner diameter of the electrodes is generally about 20 to 500 microns. When the detector is used with a gas chromatograph, the inner diameter of the electrode is preferably about equal to the inner diameter of the gas chromatograph column.

The electrodes are made of a material that conducts electricity and that can be formed into tubing with the desired inner diameters. The electrodes are preferably made of metal, and are most preferably made of stainless steel. The metal may be coated with an inert chemical to help system performance. However, due to the short length of the device, this is often unnecessary. A dielectric tube surrounds the capillary tubing both to hold the metal tubing in place and to contain gases in the discharge gap. The dielectric tubing can be made of glass, plastic or quartz with three primary considerations. First, the dielectric must be able to withstand the voltage applied across the discharge gap without itself breaking down. Second, the dielectric must be able to withstand the temperature cycles of the detection chamber and the temperature of the discharge itself. And third, if optical properties are to be examined (perpendicular to the detector), the dielectric must be able to transmit the frequency of light of interest.

A discharge is formed in the gas in the gap between the electrodes by applying voltage between the two electrodes. The gas detector is generally operated with direct current (DC) or alternating current (AC) power supplies capable of generating about 100 to 1000 volts at about 0.3 milliamps (mA) of current. The volume of the discharge ranges from about 100 picoliters (pl) to about 100 nanoliters (nl) and consumes very little power, typically about 50 microwatts ($\mu$W) to about 100 milliwatts (mW).

When used with a gas chromatograph instrument, gas exiting the column flows through the detector. A voltage sufficient to sustain a current in the gas within the discharge region is applied between the inlet and outlet ports. As a steady flow of inert gas is maintained through the device, a constant voltage will remain across the inlet and outlet ports. However, as different compounds carried with the inert gas enter the discharge region, the impedance of the gas will change affecting the discharge voltage. Monitoring these changes in voltage as a function of time gives a chromatograph.

The discharge emits light of different wavelengths which serves as an alternative or additional way to identify compounds. Each gas entering the discharge region emits characteristic light, serving as a spectral fingerprint. In order to take advantage of this additional information, a small spectrometer is added to the detector. The spectrometer is an instrument used to identify the amount of light of different colors, typically sensitive to wavelengths from 200 nanometers (nm) (in the ultraviolet spectrum) to about 1000 nm (in the infrared spectrum). A fiber optic cable is a convenient way to carry the light from the discharge to the spectrometer for analysis. Alternatively, small and inexpensive photodiodes combined with color filters can be added to the detector body to look at specific colors emitted by the discharge. This may be used when looking for only one or several compounds of interest that emit strong radiation at a specific wavelength such as sulfur or mercury. Photodiodes may be placed in close proximity to the discharge, or again, a fiber-optic cable can deliver the light from the discharge region to the photodiode.

Additional information may be obtained on the gas species within the discharge by observing the afterglow (light output) after the excitation source (current) is shut off. Some atoms and molecules continue emitting light for several microseconds after the discharge ends. The length of time and the color of light given off is another signature of the gas species within the discharge and can also be used to gain insight to the quantity and type of gas in the discharge. Thus, a repeated pulse of power may be applied to the discharge and light can be monitored not only during the main discharge but in the afterglow as well. Another way to observe the afterglow of the gas is to monitor light emission in the flow of gas downstream of the discharge. Gas flow rates through the detector range from about 5 to 50 cc/minute. If the gas flow is 10 cc/minute and the tube diameter is 200 microns, then the flow rate is approximately 1.1 mm/millisecond. Thus, drilling a small hole in the side of the electrode tube 5.5 mm from the end can serve as a port to observe light emission from gas 5 milliseconds after it exits the discharge.

Several operational parameters have been found to be very important in reducing noise in order to achieve high sensitivity. First, the capillary tubing diameter must be chosen based on the desired operating gas pressure in the discharge. Improper choices will cause time-dependent spatial modes in the discharge which result in voltage changes not dependent on gas composition. In general, the capillary diameter must decrease as the gas pressure is increased. Second, the power supply impedance must be large enough to have good sensitivity. However, an impedance that is too large will cause the discharge to extinguish in some instances. A good choice is having a power supply impedance equal to or larger than the discharge impedance. Third, the total gas pressure in the discharge region will change the electron energy distribution function and the result is a change in sensitivity for selected molecules. Finally, the temperature must be maintained to prevent thermal-induced voltage changes.

One of the primary benefits of the gas detector of this invention is its small size. The preferred embodiment shown in FIG. 1 has a length of about two centimeters and a diameter of about one centimeter. This can be further miniaturized by reducing the size of the ceramic body holding the device together. Along with small size comes light weight, and combined with the inherent low power consumption (suitable for battery power), this detector is especially adapted for use with portable gas chromatograph instruments. In operation at atmospheric pressure, the gas detector typically consumes about 0.2 milliamps (mA) at 180 volts with a helium carrier gas. Thus, a small battery powered supply using only 40 milliwatts of power can keep the device in operation for more than about 24 hours. Another advantage of its small size is that the gas detector can operate in a stable manner at atmospheric pressure. Larger diameter devices (greater than about 200 microns) tend to exhibit instability in the discharge which results in noise, limiting the sensitivity. Atmospheric pressure operation is an advantage since external pumps are not required as they are in several competing detector technologies.

If a pump is used to decrease the operating pressure of the discharge, the optical radiation emitted from the discharge will have a reduced linewidth. This often produces more atomic and molecular peaks within a given wavelength range. The additional peaks give more detailed information about the components in the discharge and may allow simultaneous detection of several different components. In other words, the number of components that can be identified is increased in the case where several components are present in the discharge at the same time.

Unlike detectors such as flame ionization detectors, this detector has no dilution of the gas exiting the column. Flame ionization detection involves mixing hydrogen and air (or oxygen) with the column effluent before igniting this mixture. Thus the column flow (30 mmin typical for a packed column) is mixed with hydrogen and air (500 mmin typical combined) diluting the gas being detected by a factor of 17. The dilution is even worse with capillary columns where a makeup gas (nitrogen typically) is mixed with the column. In this case the gas exiting the column is diluted by a factor of 180 before detection. In contrast the gas detector of this invention forms a discharge directly in the gas exiting the column without diluting the percentage of trace compounds within the gas. In addition, all associated equipment such as flow controllers, hydrogen and air filters, and a hydrogen source are eliminated, thus reducing the complexity, weight and size of the instrument. A small lecture bottle of helium (3.5 pounds holding 50 liters of gas) can supply enough carrier gas for continuous operation in excess of 80 hours.

A fiber-optic cable (or multiple fibers) can be inserted into holes drilled in the body of the detector to transmit light from the discharge to various equipment such as a spectrometer or photodiode for spectral analysis. In fact, an array of fibers in close proximity to the discharge can gather information about different parts of the discharge all at the same time. Optical fibers can be smaller than one micron core diameter to larger than 100 microns. Since the discharge length is approximately 10 to 100 microns, optical fibers are of the proper size for use with the current invention. Fibers also have the property to filter light they collect. Thus, the proper choice of fiber diameter and material can serve as a filter to block light that is not of interest.

Hollow conductive electrodes cause the device to have some unique operating characteristics. Proper choice of electrode diameter and operating pressure cause the discharge in the cathode to operate in the hollow cathode discharge mode. This creates high energy ballistic electrons within the cathode. In addition there is a positive column discharge between the cathode and anode. Thus excitation of a gas in the discharge is achieved in different ways depending on position.

The detector can be used without the column for gas analysis as a "stand alone" gas detector. If the detector is inserted into the flowing gas of a smoke stack, for instance, the flow of gas would travel through the device and enter the discharge region where spectral analysis would serve to identify the chemical species and the concentration of a desired species within the smoke stack.

If a means of injecting a microdroplet of fluid were introduced, liquid samples could also be analyzed directly in the discharge. An ink-jet printer head is capable of ejecting micron diameter sized droplets of fluid. A hole drilled through the dielectric tube, perpendicular to the gas flow, could serve as a means of introduction of the droplet into the discharge. As the droplet enters the discharge, it will be vaporized and optical emission from the vapors in the discharge can serve as compound identification to the constituents in the liquid. One application would be to inject automotive oil into the discharge to identify the concentration and type of metal for engine performance assessment. Also, water could be injected in the same manner to check for impurities or contaminants such as mercury.

When trace chemical detection is desired, several techniques can be used to increase the sensitivity. For instance, explosives detection involves looking for trace impurities of one part in $10^{14}$. For these sensitivities, the gas being analyzed is passed over a material which absorbs the chemical of interest for several seconds or minutes. The material is subsequently heated to release the absorbed compounds at a much higher concentration than in the air being tested. This is a concentration technique which could be added to the input gas stream to improve system performance for demanding applications such as explosives detection or other trace airborne contaminants.

The detector may also be placed on a mobile platform (such as a remote controlled airplane) such that it can be transported to remote locations for chemical detection. This may be useful for organizations such as the military for early warning detection systems for approaching threats. The detector is ideal for this purpose since an entire system can be made which weighs less than about four pounds and consumes less than a watt of power and uses little space (under 200 cubic inches). The detector can be manufactured at a relatively low cost so the loss of such a mobile platform in flight would be tolerable.

I claim:

1. A two electrode gas detector which is axially symmetrical along the horizontal axis comprising:
   (a) two, and only two, capillary tubing electrodes through which a gas flows, each electrode having an inner end and an outer end, the inner ends of the electrodes being coaxial and separated by a gap of 10 to 1000 microns, the outer end of one of the electrodes forming a gas inlet;
   (b) a coaxial dielectric tube spaced apart from and surrounding the electrodes axially;
   (c) a means for applying a sufficient continuous voltage across the gap between the electrodes to create a continuous plasma discharge within the gas; and
   (d) a means for measuring a change in optical properties of the gas as it passes through the gap between the electrodes.

2. The gas detector of claim 1 wherein the electrodes are nonoverlapping.

3. The gas detector of claim 1 wherein the electrodes are made of a metal coated with an inert chemical.

4. The two electrode gas detector of claim 1 wherein the means for measuring a change in optical properties of the gas comprises measuring a change in light emission.

5. The two electrode gas detector of claim 3 wherein the means for measuring a change in the light emission comprises a fiber optic cable to carry light from the discharge.

6. The two electrode detector of claim 1 additionally comprising: e) a means for generating a chromatograph.

7. The two electrode gas detector of claim 6 additionally comprising: (f) a heater.

8. The two electrode gas detector of claim 1 wherein the voltage means provides about 100 to 1000 volts across the gap between the electrodes.

9. The two electrode gas detector of claim 8 wherein the electrodes have an inner diameter of about 20 to 500 microns.

10. The two electrode gas detector of claim 9 wherein the dielectric tube is made of glass, plastic, or quartz.

11. A gas chromatograph comprising:
    (a) an injection chamber for introducing a sample;
    (b) a column separator through which the sample flows as a gas; and
    (c) a two electrode gas detector which is axially symmetrical along the horizontal axis for detecting the gas exiting the column separator, the two electrode gas detector comprising:
        (i) two, and only two, capillary tubing electrodes through which the gas flows, each electrode having an inner end and an outer end, the inner ends of the electrodes being coaxial and separated by a gap of 10 to 1000 microns, the outer end of one of the electrodes forming a gas inlet;
        (ii) a coaxial dielectric tube spaced apart from and surrounding the electrodes axially;
        (iii) a means for applying a sufficient voltage across the gap between the electrodes to create a continuous plasma discharge within the gas, and;
        (iv) a means for measuring a change in optical properties of the gas as it passes through the gap between the electrodes.

12. The gas chromatograph of claim 11 wherein the electrodes are non-overlapping.

13. The gas chromatograph of claim 11 wherein the electrodes are made of a metal coated with an inert chemical.

14. The gas chromatograph of claim 11 wherein the means for measuring a change in optical properties of the gas comprises measuring a change in light emission.

15. The gas chromatograph of claim 14 wherein the means for measuring a change in light emission comprises a fiber optic cable to carry a light from the discharge.

16. The gas chromatograph of claim 11 wherein the two electrode gas detector additionally comprises: (v) a means for generating a chromatograph.

17. The gas chromatograph of claim 16 wherein the two electrode gas detector additionally comprises: (vi) a heater.

18. The gas chromatograph of claim 11 wherein the voltage means provides about 100 to 1000 volts across the gap between the electrodes.

19. The gas chromatograph of claim 18 wherein the electrodes have an inner diameter of about 20 to 500 microns.

20. The gas detector of claim 19 wherein the dielectric tube is made of glass, plastic, or quartz.

* * * * *